United States Patent [19]

Cho et al.

[11] Patent Number: 5,502,226
[45] Date of Patent: Mar. 26, 1996

[54] PROCESS OF PREPARING ω-HYDROXY ACIDS

[75] Inventors: Suk H. Cho, Bogota; Victor DeFlorio, Belleville, both of N.J.

[73] Assignee: Elizabeth Arden Co., Division of Conopco, Inc., New York, N.Y.

[21] Appl. No.: 338,300

[22] Filed: Nov. 14, 1994

[51] Int. Cl.$^6$ .................................................. C07C 51/00
[52] U.S. Cl. ........................................... 554/154; 554/124
[58] Field of Search ..................................... 554/124, 154

[56] References Cited

U.S. PATENT DOCUMENTS

| | | | |
|---|---|---|---|
| 5,099,036 | 3/1992 | Yoshida et al. | 549/321 |
| 5,191,096 | 3/1993 | Yokota et al. | 554/129 |

FOREIGN PATENT DOCUMENTS

| | | | |
|---|---|---|---|
| 2126892 | 4/1984 | United Kingdom . | |
| 93/22281 | 11/1993 | WIPO . | |

OTHER PUBLICATIONS

Heslinga, L. et al., "Synthesis of the linoleic acid esters of some unsaturated long–chain ω–hydroxy fatty acids," *Recl. Trav. Pays–Bas*, 103, pp. 348–351 (1984).

Ames, D. E. et al., "Syntheses of Long–chain Acids. Part III. 9,10,18–Trihy–droxyoctadecanoic Acids", *J. Chem. Soc.* (C) 1967, pp. 1556–1558.

*Primary Examiner*—José G. Dees
*Assistant Examiner*—Deborah D. Carr
*Attorney, Agent, or Firm*—Rimma Mitelman

[57] ABSTRACT

A new synthesis of ω-hydroxy acids, which employs commercially available starting materials and lowers the cost of production. The process involves coupling a fatty acyl group by enamine chemistry, followed by a ring expansion and selective reduction of ketoacid.

17 Claims, No Drawings

PROCESS OF PREPARING ω-HYDROXY ACIDS

FIELD OF THE INVENTION

The invention relates to a new synthesis of ω-hydroxy acids.

BACKGROUND OF THE INVENTION

ω-hydroxy acids are valuable intermediates in manufacture of ceramide 1. Ceramides are lipids found in skin which form a water barrier in skin preventing water loss from the skin. Several species of natural ceramides have been identified. Ceramide 1 is one of the major ceramides found in skin. Ceramide 1 must be obtained either through a lengthy process involving the extraction of the ceramide from natural sources or via a synthetic route. Synthetic routes to ceramide 1 involve reacting an ω-hydroxy acid with sphingosine and linoleic acid. See e.g., WO 93/22281 (Unilever). A cost-effective synthesis of ω-hydroxy acids is desirable, in order to lower the cost of ceramide 1 manufacture.

ω-hydroxy acids may also be used in skin treatment and cosmetic compositions, without prior conversion to ceramides. Recent research demonstrates that topical application of ω-hydroxy acids stimulates ceramide production in the epidermis, leading to an increase in the level of ceramides in the skin.

ω-hydroxy acids are also key raw materials in the manufacture of fragrances and various polymers.

An ω-hydroxy acid may be obtained naturally or by a synthetic route.

WO 93/22,28 discloses the synthesis of ceramide 1 and ω-hydroxytricotanoic acid. ω-hydroxy acid is prepared by reacting 1,7-octadiyne in THF which was treated with HMPA, BuLi, and 11-bromoundecanol to give 1,30-hydroxytriaconta-12,18-diyne in low yield. The diyne was then hydrogenated to give 1,30-tricotanediol, in which one hydroxy group was protected and the other hydroxy group was oxidized to a carboxylic acid. This last step in the process disclosed in the '281 document is an unselective protection and gives desired intermediate in low yield: the process also uses expensive raw materials.

Heslinga and Pabon describe ω-hydroxy docosanoic acid synthesis in "Synthesis of the linoleic acid esters of some unsaturated long-chain ω-hydroxy fatty acids," *Recl. Trav. Pays-Bas*, 103, pp. 348–351 (1984). Their synthesis requires the use of 11-undecynoic acid, which can be obtained by reacting sodium acetylide with 9-iodononanoic acid. 11-undecynoic acid is converted to 11-bromoundecynoic acid using hydrobromination. THP protected acetylide, 1-0-tetrahydropyranyl-10-undecyne is prepared by using tetrahydropyran as protecting group as described by Parham et al., J. Am. Chem. Soc. (1948) 70, 4187, and subsequently is reacted with 11-bromo-10-undecynoic acid to give a diacetylene adduct. Hydrogenation followed by a deprotection of THP gives ω-hydroxy docosanoic acid.

Yokota et al. (U.S. Pat. No. 5,191,096) discloses a process of subjecting an ester or a di-carboxylic acid compound to a catalytic hydrogenation. Dioic acid is disclosed as a suitable starting material. Unfortunately, only a few dioic acids are commercially available. Hirosi et al. (U.S. Pat. No. 5,099,036) discloses a process of making α-(ω-cyanoalkanoyl)-γ-butrylactone. The processes disclosed by Yokota and Hirosi consist of complicated and multistage production steps, and expensive raw materials are used, so that the production cost is unfavorable. The Hirosi process is also limited to shorter carbon chain length (i.e., 7 to 12 carbons) due to poor availability of raw materials and cyanoalkanoyl materials.

The above-discussed processes have serious shortcomings: they require multiple steps and expensive raw materials.

Naturally occuring ω-hydroxy docosanoic acid has been isolated from the outer bark of Betula verrucosa Ehrh. by hydrolysis, methanolysis, and alkali fusion. About 14% of ω-hydroxy docosanoic acid is identified in the dried outer barks. ω-hydroxy docosanoic acid was also isolated from a typical cork tree. Obtaining ω-hydroxy acid from natural sources is tedious and expensive.

As evidenced by the art discussed above, there is a need for an alternative, commercially viable process of making an ω-hydroxy acid.

Accordingly, it is an object of the present invention to provide a novel process of preparing an ω-hydroxy acid while avoiding the disadvantages of prior art.

These and other objects of the invention will become more apparent from the detailed description and examples that follow.

SUMMARY OF THE INVENTION

The above objects are attained by the present invention which includes a process of making an ω-hydroxy acid.

According to the present invention, two essentially similar processes are disclosed (Process A and Process B).

Processes A and B according to the present invention are generally represented by the flow diagrams, as follows:

Process A:

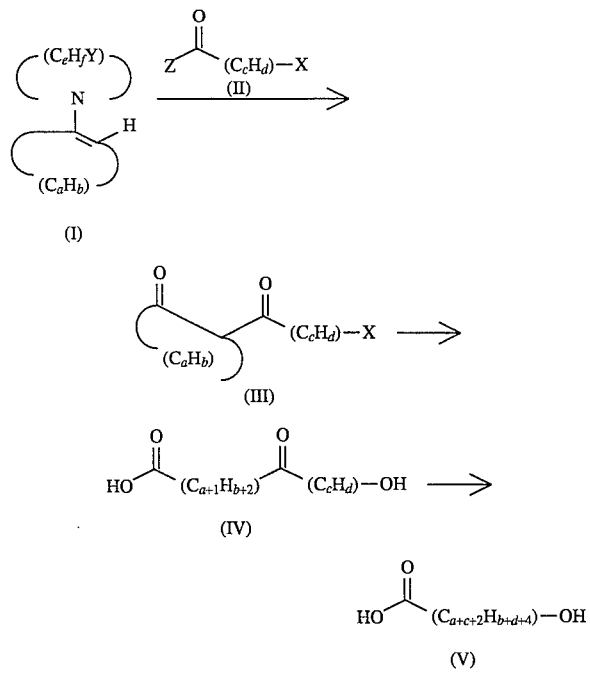

Process B:

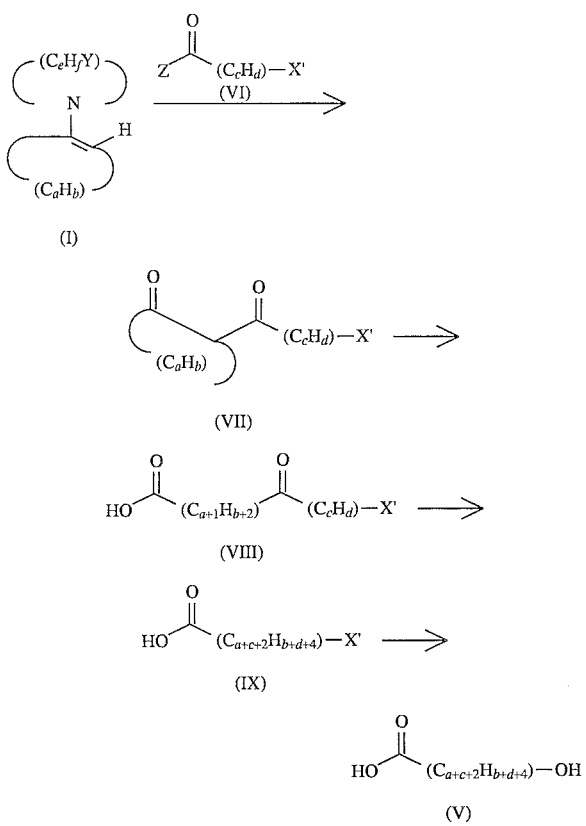

The difference between Processes A and B stems from the fact that an enamine of Formula I is reacted with compound of Formula II in Process A; whereas in Process B the enamine is reacted with a compound of Formula VI. Compounds II and VI are essentially the same, with the only difference that compound II carries an X substituent which is selected from —OH, and good leaving groups such as a halogen atom, OTs, and OMs, whereas compound VI carries X' substitute which is an alkyl or aryl ether.

The first six steps of inventive Processes A and B are identical. In step (i) an anhydrous mixture is prepared of (a) an enamine heaving Formula I:

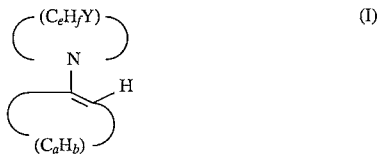

wherein
a is an integer from 1 to 20
b is an integer from 2 to 40,
e is an integer from 4 to 12,
f is an integer from 4 to 24, and
Y is oxygen, nitrogen, or —$CH_2$;

(b) a compound having Formula II (Process A) or a compound having Formula VI (Process B)
wherein
c is an integer from 1 to 30,
d is an integer from 2 to 60,
Z is a good leaving group, e.g., a halogen atom, OMs, OTs, X is selected from the group consisting of —OH, a halogen atom, OTs and OMs, X' is an alkyl ether or an aryl ether group containing from 1 to 20 carbon atoms, preferably from 1 to 12 carbon atoms, most preferably from 7 to 10 carbon atoms. Alkyl or aryl group may be linear or substituted. The most preferred X' substituent is selected from benzylic analogs which can be easily removed by simple hydrogenation; and (c) a base catalyst.

According to the inventive processes, the molar ratio of the enamine to the compound of Formula II or a compound having Formula VI is generally in the range of from about 1:1 to about 1:2.

The resulting mixture is reacted at a temperature in the range of from about 20° C. to about 150° C., to obtain a first reaction solution. The reaction is monitored by TLC or GC or HPLC for the disappearance of starting materials. The reaction is typically stopped at a point when from 80% to 100% of starting material has disappeared. The first reaction solution is then quenched with aqueous acid (acid and water) and subsequently refluxed to obtain a second reaction solution containing a diketone of Formula III (Process A) or a diketone of Formula VII (Process B). The diketone is mixed and refluxed with a hydroxy-containing inorganic base, in a solvent, to obtain a ketoacid of Formula IV (Process A) or a ketoacid of Formula VIII (Process B). According to the inventive Process A, reduction (e.g., Wolff-Kischner reduction) of the resulting ketoacid results in an ω-hydroxy acid having Formula V. According to the inventive Process B the same reduction step results in a compound having Formula IX, which is subsequently hydrogenated or deprotected to obtain an ω-hydroxy acid of Formula V.

The inventive processes may be employed to produce a wide range of ω-hydroxy acids of Formula V, wherein a is an integer from 1 to 20, c is an integer from 1 to 30, b is an integer from 2 to 40, d is an integer from 2 to 60. Preferably, the a+c+2 is 10 to 40, most preferably 12 to 35. Preferably, b+d+4 is 10 to 80 most preferably 12 to 70. ω-hydroxy acid can subsequently be converted into an ester or a salt or a cyclic lactone using reactions known in the art. ω-hydroxy acids of Formula V may be linear or branched, and may contain phenyl or aryl groups, or ether or a hydroxyl moiety.

DETAILED DESCRIPTION OF THE INVENTION

According to the present invention, the preferred process is Process A because it is more cost-effective than Process B.

The first step of both inventive processes A and B involves the preparation of an anhydrous mixture containing an enamine having Formula I, a compound having formula II(Process A) or a compound having Formula VI(Process B), and a base catalyst. The molar ratio of the enamine to the compound having Formula II or to the compound having Formula VI is in the range of from about 1:1 to about 1:2, preferably from about 1:1 to about 1:1.5, most preferably the ratio is 1:1, in order to lower cost. In the preferred embodiment of the invention, in the enamine having Formula I, a is an integer from 3 to 16, most preferably from 4 to 12, b is preferably an integer from 4 to 32, most preferably from 6 to 24, e is preferably an integer from 4 to 10, most preferably from 4 to 6, f is preferably an integer from 4 to 20, most preferably from 4 to 12, and Y is —$CH_2$ or oxygen. These values and substitutes are preferred in order to lower cost by using readily available starting materials to attain the preferred starting enamines.

In the compound having Formula II or Formula VI, c is an integer from 1 to 30, preferably from 3 to 25, most preferably from 8 to 20; d is an integer from 2 to 60, preferably from 6 to 50, most preferably from 8 to 40; X is Cl or Br; X' is benzyloxy, and Z is Cl or Br.

The base catalyst is alkyl- or arylamine. Suitable examples of the base catalyst include but are not limited to triethylamine, tributylamine, or pyridine. The preferred base catalyst is an organic base in order to attain a more homogeneous mixture. In the preferred embodiment of the invention, the anhydrous mixture prepared in step (i) of inventive processes further comprises a drying agent, e.g., molecular seive, calcium sulfate or calcium carbonate. Further, the preparation of an anhydrous mixture (step i) and the subsequent reaction (step ii) of the inventive processes are preferably carried out under an inert gas blanket, e.g., nitrogen blanket, in order to attain higher yields. Preferably, the starting materials, i.e., the enamine having Formula I and compound II or compound VI are liquid and the subsequent reaction is conducted "neat", i.e., in the absence of the solvent. However, if the starting materials are not liquid and organic solvent is required, suitable organic solvents include but are not limited to THF, DME, ether, methylene chloride, chloroform, toluene, cyclohexane, xylene. Preferably, in order to keep the mixture anhydrous, the solvent is degassed.

Preferably, the anhydrous mixture in step 1 is prepared in two steps: first, adding with stirring the base catalyst to the enamine, and subsequently adding to the resulting mixture the compound of Formula II (Process A) or Formula VI (Process B).

In the second step of inventive processes, the anhydrous mixture prepared in step (i) is reacted in order to attain a first reaction solution. Generally, the reaction is carried out at a temperature in the range of from about 20° C. to about 150° C. Preferably, the temperature is in the range of from about 20° C. to about 100° C., most preferably from about 50° C. to about 60° C., in order to facilitate the reaction and increase the yield. The resulting reaction solution is hydrolyzed by quenching with an aqueous acid and refluxing to obtain a second reaction solution containing a diketone having Formula III (Process A) or Formula VII (Process B). An acid employed in step (iii) of the inventive processes is any acid. Suitable examples of acids include but are not limited to HCl, $H_2SO_4$, $H_3PO_4$, polyphosphoric acid, HOAc, and Dowex H® resin. The ratio of the acid employed in step (iii) of the inventive processes to the compound of Formula I is in the range of from about 0.1:1 to about 0.1:4, preferably from about 0.5:1 to about 0.5:2, most preferably from about 1:1 to about 1:2. Step (iii) of the inventive processes is conducted by adding the aqueous acid to the reaction solution obtained in step (ii) and stirring the resulting solution, typically for about 48 hours, preferably 2 to 6 hours while monitoring formation of product or disappearance of starting materials. The resulting diketone of Formula III (Process A) or Formula VII (Process B) is mixed with a hydroxy-containing inorganic base in a solvent to obtain a third reaction solution. Suitable hydroxy-containing inorganic base include, but are not limited to alkali or alkaline earth metal hydroxides (e.g., NaOH, KOH, $Ca(OH)_2$). The preferred inorganic base is NaOH or KOH. The ratio of diketone to hydroxy-containing inorganic base is in the range of from about 1:1 to about 1:6, preferably from about 1:1 to about 1:4, most preferably from about 1:1 to about 1:3. The solvent employed in step (iv) of the inventive processes is preferably a polar solvent such as water or an alcohol (e.g., methanol, ethanol, etc.). The preferred solvent is methanol, due to its low cost and enhanced solubilizing effect. In step (v) of the inventive processes, the solution which results in step (iv) of inventive processes is refluxed for 1 to 48 hours, preferably 1 to 24 hours, most preferably 4 to 8 hours to obtain a fourth reaction solution containing a ketoacid having Formula IV (Process A) or Formula VIII (Process B).

In step (vi) of the inventive processes, the resulting ketoacid is reduced. Any selective reduction of the ketone group to methylene group without reducing carboxylic acid is suitable. The preferred method of reducing the diketone in step (vi) of the inventive processes is a Wolff-Kischner reduction. The Wolff-Kishner reduction is an effective selective reduction of ketone group to methylene group which involves the base catalyzed decomposition of hydrazones. Alkyl diimides are believed to be formed and the loss of nitrogen results in the selective reduction process. In the Wolff-Kishner reduction, a base and aqueous hydrazine and ketoacid are mixed in the presence of solvent and then refluxed to make hydrazone intermediate. Excess hydrazine is then removed by distillation. Subsequent refluxing induces base-catalyzed decomposition of hydrazone resulting in compound V (Process A) or compound IX (Process B). If Wolff-Kischner reduction is employed, ketoacid to base ratio is in the range of from 1:1 to 1:6, preferably from 1:1 to 1:4, most preferably from 1:2 to 1:4 in order to improve yield. Suitable solvents to be employed in the reduction include diglyme, water, DME, ethylene glycol, any hydroalcohol and mixtures thereof. Ketoacid to hydrazine ratio is in the range of from 1:1 to 1:8, preferably from 1:1 to 1:6, most preferably from 1:2 to 1:4. Reflux time is 1 to 48 hours, preferably 1 to 24 hours, most preferably 1 to 4 hours. Subsequently, excess hydrazine is removed by distillation before further refluxing.

Other suitable reductions are Clemenson reduction, Calglioti reduction, thioketal desulfurization, cathode reduction. Wolff-Kischner reduction is preferred, because it is more effective and thus it is economically favorable.

The reduction of the ketoacid in step (vi) of inventive Process A, results in obtaining an ω-hydroxy acid having Formula V. However, when Process B is employed, an additional step involving hydrogenation or deprotection of the compound having Formula IX must be carried out. Suitable solvents for hydrogenation include but are not limited to alcohols, ether, water. Methyl or ethyl alcohol is most preferred. The hydrogenation is performed under $H_2$ blanket with transition metal catalysts, e.g., Pd/C. The pressure employed in hydrogenation is in the range from a normal atmospheric pressure to high pressure. The temperature is in the range of from 20° C. to 100° C., more preferably from about 20° C. to 80° C., most preferably from about 20° C. to 50° C. The hydrogenation is conducted for 1–72 hours, most preferably 6–24 hours.

Any ω-hydroxy acid which falls within Formula V may be synthesized according to inventive processes A and B. Examples of ω-hydroxy acids that may be synthesized include, but are not limited to:
6-hydroxy hexanoic acid
7-hydroxy heptanoic acid
8-hydroxy octanoic acid
9-hydroxy nonanoic acid
10-hydroxy decanoic acid
11-hydroxy undecanoic acid
2,25-dihydroxy dihydroxy pentacosanoic acid
12-hydroxy dodecanoic acid
14-hydroxy tetradecanoic acid
15-hydroxy pentadecanoic acid
2,9-dihydroxy dihydroxy nonanoic acid 16-hydroxy hexadecanoic acid
17-hydroxy heptadecanoic acid
18-hydroxy octadecanoic acid
19-hydroxy nonadecanoic acid
2,15-dihydroxy pentadecanoic acid
20-hydroxy eicosanoic acid
21-hydroxy heneicosanoic acid
22-hydroxy docosanoic acid
23-hydroxy tricosanoic acid
2,14-dihydroxy tetradecanoic acid
24-hydroxy tetracosanoic acid
25-hydroxy-3-methyl-pentacosanoic acid
13-hydroxy-2-methyl tridecanoic acid
27-hydroxy heptacosanoic acid
28-hydroxy octacosanoic acid
29-hydroxy nonacosanoic acid
30-hydroxy triacontanoic acid
31-hydroxy untriacontanoic acid
32-hydroxy dotriacontanoic acid
33-hydroxy tritriacontanoic acid
17-hydroxy-7-methyl heptadecanoic acid
35-hydroxy pentatriacontanoic acid
36-hydroxy hexatriacontanoic acid
37-hydroxy heptatriacontanoic acid
2,25-dihydroxy pentacosanoic acid
38-hydroxy octatriacontanoic acid
39-hydroxy nonatriacontanoic acid
40-hydroxy tetracontanoic acid
18-hydroxy-2-methyl-4-octadecenoic acid
41-hydroxy untetracontanoic acid
42-hydroxy dotetracontanoic acid
21-hydroxy-2-methyl-4-henecosanoic acid
43-hydroxy tritetracontanoic acid
44-hydroxy tetratetracontanoic acid
45-hydroxy pentatetracontanoic acid
46-hydroxy hexatetracontanoic acid
47-hydroxy heptatetracontanoic acid
48-hydroxy octatetracontanoic acid
49-hydroxy nonatetracontanoic acid
50-hydroxy pentacontanoic acid
51-hydroxy unpentacontanoic acid
52-hydroxy dopentacontanoic acid
2,6-dihydroxy hexanoic acid
13-hydroxy tridecanoic acid
2,7-dihydroxy heptanoic acid
7-hydroxy-2-methyl heptanoic acid
2,8-dihydroxy octanoic acid
8-hydroxy-2-propyl octanoic acid
17-hydroxy heptadecanoic acid
9-hydroxy-3-methyl nonanoic acid
2,10-dihydroxy decanoic acid
10-hydroxy-2-propyl decanoic acid
2,11-dihydroxy undecanoic acid
11-hydroxy-4-methyl undecanoic acid
2,12-dihydroxy dodecanoic acid
12-hydroxy-4-butyl dodecanoic acid
2,13-dihydroxy tridecanoic acid
14-hydroxy-4-methyl tetradecanoic acid
25-hydroxy pentacosanoic acid
15-hydroxy-5-methyl pentadecanoic acid
2,16-dihydroxy hexadecanoic acid
16-hydroxy-2-methyl hexadecanoic acid
2,17-dihydroxy heptadecanoic acid
26-hydroxy hexacosanoic acid
2,18-dihydroxy octadecanoic acid
18-hydroxy-5-methyl octadecanoic acid
2,19-dihydroxy nonadecanoic acid
19-hydroxy-3-methyl nonadecanoic acid
2,20-dihydroxy eicosanoic acid
20-hydroxy-2-methyl eicosanoic acid
2,21-dihydroxy heneicosanoic acid
21-hydroxy-6-methyl heneicosanoic acid
2,22-dihydroxy docosanoic acid
22-hydroxy-3-methyl docosanoic acid
2,23-dihydroxy tricosanoic acid
23-hydroxy-6-propyl tricosanoic acid 34-hydroxy tetratriacontanoic acid
24-hydroxy-2-methyl tetracosanoic acid
25-hydroxy-2-propyl pentacosanoic acid
2,24-dihydroxy tetracosanoic acid
2,26-dihydroxy hexacosanoic acid
26-hydroxy-6-methyl hexacosanoic acid
2,27-dihydroxy heptacosanoic acid
27-hydroxy-3-methyl heptacosanoic acid
17-hydroxy-2-methyl-4-heptadecenoic acid
28-hydroxy-2-methyl octacosanoic acid
2,29-dihydroxy nonacosanoic acid
29-hydroxy-9-methyl nonacosanoic acid
2,30-dihydroxy triacontanoic acid
6-hydroxy-3-hexenoic acid
7-hydroxy-5-heptenoic acid
8-hydroxy-6-octenoic acid
9-hydroxy-3-nonenoic acid
10-hydroxy-4-decenoic acid
26-hydroxy-13,16-hexacosadienoic acid
11-hydroxy-6-undecenoic acid
12-hydroxy-3-dodecenoic acid
13-hydroxy-5-tridecenoic acid
16-hydroxy-4-methyl-8,11-hexadecadienoic acid
15-hydroxy-3-pentadecenoic
18-hydroxy-9,12-octadecadienoic acid
18-hydroxy-5-octadecenoic acid
19-hydroxy-7-nonadecenoic acid
20-hydroxy-3-eicosenoic acid
18-hydroxy-4-methyl-9,12-octadecadienoic acid
22-hydroxy-4-docosenoic acid
23-hydroxy-12-tricosenoic acid
24-hydroxy-9-tetracosenoic acid
25-hydroxy-3-pentacosenoic acid
18-hydroxy-5-octadecenoic acid
28-hydroxy-3-octacosenoic acid
28-hydroxy-4-methyl-14,17-octacosadienoic acid
29-hydroxy-7-nonacosenoic acid
30-hydroxy-6-triacontenoic acid
10-hydroxy-2-methyl-4-decenoic acid
11-hydroxy-3-propyl-4-undecenoic acid
27-hydroxy-13-heptacosenoic acid
12-hydroxy-4-methyl-6-dodecenoic acid
13-hydroxy-2-methyl-4-tridecenoic acid
14-hydroxy-2-methyl-7-tetradecenoic acid
15-hydroxy-3-methyl-7-pentadecenoic acid
16-hydroxy-5-methyl-8-hexadecenoic acid
19-hydroxy-2-propyl-4-nonadecenoic acid
20-hydroxy-2-methyl-4-eicosenoic acid
22-hydroxy-2-butyl-4-docosenoic acid
2,28-dihydroxy octacosanoic acid
23-hydroxy-2-methyl-4-tricosenoic acid
24-hydroxy-2-methyl-4-tetracosenoic acid
12-hydroxy-6,9-dodecadienoic acid
14-hydroxy-7,10-tetradecadienoic acid
16-hydroxy-8,11-hexadecadienoic acid
30-hydroxy-8-methyl triacontanoic acid
20-hydroxy-10,13-eicosadienoic acid
22-hydroxy-11,14-docosadienoic acid 24-hydroxy-12,15-tetracosadienoic acid
14-hydroxy-7-tetradecenoic acid
28-hydroxy-14,17-octacosadienoic acid
30-hydroxy-15,18-triacontadienoic acid
12-hydroxy-4-methyl-6,9-dodecadienoic acid
14-hydroxy-4-methyl-7,10-tetradecadienoic acid
17-hydroxy-3-heptadecenoic acid
20-hydroxy-4-methyl-10,13-eicosadienoic acid
22-hydroxy-4-propyl-11,14-docosdienoic acid
24-hydroxy-4-methyl-12,15-tetracosadienoic acid
26-hydroxy-4-butyl-13,16-hexacosadienoic acid
26-hydroxy-16-hexacosenoic acid
21-hydroxy-10-heneicosenoic acid
30-hydroxy-4-methyl-15,18-triacontadienoic acid.

The following specific examples further illustrate the invention, but the invention is not limited thereto.

EXAMPLES

Methods and Materials

Proton and carbon magnetic resonance spectra were recorded on a Bruker AC 200 model spectrometer. Chemical shifts are reported in parts per million downfield from tetramethylsilane as an internal standard. Coupling constants (J value) are given in hertz (Hz) and spin multiplicities are indicated as follows: s (singlet), d (doublet), t (triplet), q (quartet), m (multiplet) and br (broad). The deuterated NMR solvents contain 99.0–99.8% deuterium in the indicated position, and were purchased from Cambridge Isotope Laboratories.

Infrared spectra were recorded on a Perkin-Elmer model 298 spectrometer using a NaCl cell. Peak positions are listed in $cm^{-1}$ as vs (very strong), s (strong), m (medium), w (weak), or br (broad).

Differential scanning calorimetry experiments were performed on a Dupont DSC with a 2910 cell base and 2100 thermal analyst. Samples of approximately 1 mg were accurately weighed into aluminum pans which were then hermetically sealed. After equilibration to 30° C., the samples were heated at a rate of 5° C./minute.

Fast atom bombardment mass spectra were performed on a Finnigan MAT TSQ70 mass spectrometer under chemical ionization conditions.

Gas chromatography (GC) was performed using a Hewlett Packard 5840A gas chromatograph which contained a 25M×0.2 mm HP-1 column. The column was coated with phenyl methyl silicone at a thickness of 0.33 μm. The GC parameters were as follows: Inj. temp.=250° C., initial column temp.=70° C., rate=15° C./minute, final column temp.=250° C.

All solvents were reagent grade quality and were used as received. All reagents were purchased from the Aldrich, Sigma or Lanchaster Synthesis chemical companies and were used as received.
Purification assessment:

In most cases, a small sample was converted to the methyl ester/trimethyl silyl ether and analyzed by gas chromatography. Also, a higher temperature thermoprobe in FAB/MS instrument was used to determine the purifity of samples.

EXAMPLE 1

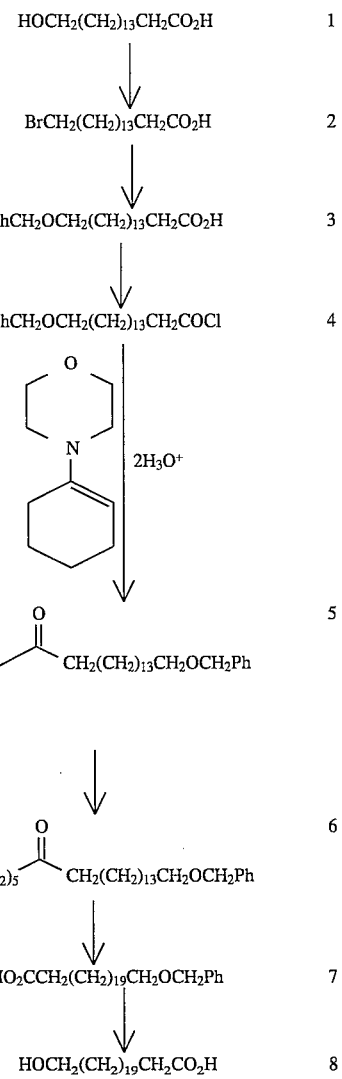

Synthesis of 16-Hydroxy Hexadecanoic Acid (Juniperic acid:) 1

A 5 liter three neck round bottom flask, equipped with a mechanical stirrer and reflux condenser, was charged with 300 g (1.16 moles) of 99% hexadecanolide, 1000 mls of 50% sodium hydroxide, 1500 mls of toluene and 5.6 g (0.01 6 moles) of 97% tetrabutylammonium hydrogen sulfate. The reaction mixture stirred at 85°–95° C. overnight, the reaction was cooled, and filtered under vacuum. The filtered solid was washed with diethyl ether before being added to water and acidified to pH=1.5 with concentrated hydrochloric acid. The precipitated product was filtered under vacuum, washed several times with water and dried at 50°–60° C. under high vacuum to give 353 g (1.2 moles) of 97% 16-hydroxy hexadecanoic acid.

Yield: 97 % Purity: >97% Melting Point: 94°–95° C. DSC=95.5° C. (sharp) IR (nujol mull): 3250 (br), 1690 (s) $^1$H NMR (200 MHz, $CDCL_3$): δ3.6 (t, 2H), 2.3 (t, 2H), 1.6 (br. s, 4H), 1.3 (br. s, 22H)

Synthesis of 16-Bromohexadecanoic Acid 2

A 2 liter three neck round bottom flask, equipped with a mechanical stirrer, reflux condenser and nitrogen inlet, was charged with 177 g (0.63 moles) of 16-hydroxy hexadecanoic acid 1. To this vessel were added 1000 mL (5 moles) of 30% hydrogen bromide in acetic acid and 310 mL of concentrated sulfuric acid. The system was equipped with sequential traps containing a sodium hydroxide pellet trap, a 25% aqueous sodium hydroxide solution trap and a saturated sodium carbonate trap. The reaction stirred overnight at room temperature before it was heated to reflux for six hours. The reaction mixture was cooled, poured over ice water and the precipitated solid was filtered under vacuum. After drying under high vacuum, 196 g of 16-bromohexadecanoic acid was obtained.

Yield: 88% Purity: >95% Melting Point: 67°–69° C. DSC=69.0° C. (sharp) IR (nujol mull): 1700 (s), 650 (s) $^1$H NMR (200 MHz, $CD_2CL_2$): $\delta$3.4 (t, J=8 Hz, 2H), 2.3 (t, J=8 Hz, 2H), 1.8 (m, 2H), 1.6 (m, 2H), 1.2 (br. s, 22H)

Synthesis of 16-Benzyloxy Hexadecanoic Acid 3

A clean, oven dried 5 liter four neck flask, equipped with a mechanical stirrer, a reflux condenser and a 250 mL dropping funnel, was charged with 100 g (2.67 moles) of 60% sodium hydride (dispersion in mineral oil) and 5.1 g (0.17 moles) of 80% sodium hydride (dispersion in mineral oil). The solid was washed twice with 1000 mL of hexane before 3000 mL of anhydrous toluene were added. 147 g (1.36 moles) of anhydrous benzyl alcohol were charged into the dropping funnel and the benzyl alcohol was slowly added to the stirring sodium hydride solution at room temperature over a 75 minute period. Upon completion of the addition, the reaction was heated to 50° C. for one hour before the temperature was increased to 70°–75° C. At this point, the addition funnel was removed and 381 g (1.09 moles) of 16-bromohexadecanoic acid 2 were added manually through a funnel with a slight exotherm developing.

After refluxing for 48 hours, the toluene was removed under vacuum, water was added and the pH was adjusted to 1.0 with concentrated sulfuric acid. The resulting tan precipitate was filtered off under vacuum and washed several times with water before it was dried under high vacuum at 40°–50° C. for several days. After drying, 388 g of 16-benzyloxyhexadecanoic acid were obtained.

Yield: 93% Purity: >95% Melting Point: 56°–59° C. DSC=57.2° C. (sharp) IR (nujol mull): 1710(s), 1110(m) $^1$H NMR (200 MHz, $CDCL_3$): $\delta$7.3 (br. m, 5H), 4.5 (s, 2H), 3.4 (t, J=6 Hz, 2H), 2.3 (t, J=8 Hz, 2H), 1.6 (br. s, 4H), 1.2 (br. s, 22H)

Synthesis of 16-Benzyloxy Hexadecanoyl Chloride 4

Into a clean, oven dried 5 liter three neck flask equipped with a stir bar and reflux condenser, were charged 387 g (1.02 mole) of 16-benzyloxy-hexadecanoic acid. To this were added 2500 mL of anhydrous toluene, 203 g (1.71 moles) of thionyl chloride and 10 mls of pyridine. The mixture was stirred, under nitrogen, at reflux temperature overnight. When the reaction was complete, HCl and excess thionyl chloride were removed under vacuum at 40°–50° C. The vacuum was provided by a diaphram pump with an in line trap containing sodium hydroxide pellets. After the excess thionyl chloride was removed, the majority of toluene was distilled off under vacuum leaving a concentrated acid chloride solution. Yield was nearly quantitative.

IR (neat): 1800 (s)

Synthesis of 2-(15-Benzyloxyhexadecanoyl)-cyclohexanone 5

Into a clean, dry 5 liter four neck flask, equipped with a mechanical stirrer, condenser, thermometer and a 1 liter dropping funnel, were charged 190 g (1.12 moles) of 98% morpholino-1-cyclohexene, 103 g (1.0:2 moles) of triethylamine and 1000 mL of anhydrous toluene. The concentrated acid chloride solution was transferred into the dropping funnel under positive nitrogen pressure via a 12 gauge canula. This solution was added dropwise, under nitrogen, to the reaction flask at 40°–50° C. over a four hour period. The reaction mixture then stirred at 50°–60° C. overnight.

The following morning, 1000 mL of 20% hydrochloric acid were directly added to the reaction flask and the reaction mixture refluxed for about 6 hours. The reaction was cooled and continued to stir at room temperature overnight. Toluene and water were distilled off under vacuum at 40°–50° C. before the flask was put under high vacuum at 450° C. to remove any remaining toluene and water. 2 liters of methylene chloride were added to the flask containing the solid product and the mixture was stirred for 30 minutes. The mixture was transferred to a 4 liter separatory funnel and extracted three times with 1000 mls of water. The combined water layers were brought to pH=6 with 25% sodium hydroxide and extracted twice with methylene chloride. The combined methylene chloride layers were dried over magnesium sulfate and filtered under vacuum. The filtrate was concentrated under vacuum to give 420 g of crude product.

Crude yield: 93%

One liter of 60/40 hexane/ether was added to the flask containing the crude product and the mixture was heated at 40° C. until homogeneous. The solution was poured through a two liter medium fritted funnel which contained silica gel wetted with hexane. The concentrated filtrate was dissolved in two liters of warm (50° C.) hexane and refiltered through fresh silica gel. The resulting filtrate was concentrated to give 358 g of 2-(16-Benzyloxyhexadecanoyl)-cyclohexanone.

Yield: 74% Purity: >94% FAB/MS: [M+H]$^+$443.2; [M+NH4]$^+$460.2 IR (nujol mull): 1710 (br. m), 1625 (br. s), 1110(m) 1H NMR (200 MHz, $CDCL_3$): $\delta$7.3 (br. m, 5H), 4.5 (s, 2H), 3.7 (apparent br. t, 1H), 3.4 (t, J=6 Hz, 2H), 2.3 (br. m, 4H), 1.65 (br. m, 8H), 1.3 (br. s, 24H) $^{13}$C (50 MHz, $CDCl_3$): $\delta$202.5, 182.3, 139.6, 129.1, 128.4, 128.3, 73.7, 71.4, 66.7, 37.8, 30.3, 27.1, 24.7, 23.8, 22.6

Synthesis of 22-Benzyloxy-7-ketodocosanoic Acid 6

Into a clean, dry 5 liter one neck round bottom flask, were charged 113 g (2.0 moles) of potassium hydroxide, 3000 mL of methanol and 358 g (0.73 moles) of 2-(15-benzyloxy hexadecanoyl)-cyclohexanone. The flask was equipped with a magnetic stir bar and a reflux condenser. The stirring reaction mixture was refluxed under nitrogen for 4.5 hours before being cooled and then continued to stir at room temperature overnight.

The methanol was distilled off under vacuum and the potassium salt of the keto acid was dissolved in water and acidified to a pH of about 1. The precipitated white solid was isolated by vacuum filtration and washed several times with water before being dried under high vacuum for several days.

Yield: 81% IR (nujol mull): 2620 (hr. w), 1710 (s), 1110 (m) $^1$H (200 MHz, $CDCl_3$): $\delta$7.3 (m, 5H), 4.5 (s, 2H), 3.4 (t, J=6 Hz, 2H), 2.3 (br. m, 6H), 1.6 (br. m, 8H), 1.3 (br. s, 24H)
$^{13}$C (50 MHz, CDCl$_3$): δ211.4, 180.0, 138.8, 128.3, 127.6, 127.4, 72.8, 70.5, 42.8, 42.4, 34.0, 29.6, 29.4, 26.1, 23.8

Synthesis of 22-Benzyloxydocosanoic Acid 7

To a 500 mL four neck flask containing 65 mL of anhydrous ethylene glycol, were charged 6.0 g (0.108 moles) of powdered potassium hydroxide. The flask was equipped with a mechanical stirrer, reflux condenser, thermometer and stopper. The mixture was heated to about 100° C. under nitrogen to solubilize the base before 26 g (0.048 mole) of sodium benzyloxydocosanoate were added through a powder funnel. 10.7 g (0.215 moles) of hydrazine monohydrate were added and the reaction was then heated to reflux (143° C.) for two hours. The mixture was cooled to 100° C. and the reflux condenser was replaced with a short path distillation head. At this point, the reaction vessel was wrapped in foil and heated to 150°–200° C. and about 15 mls of a hydrazine/water azeotrope were collected at a vapor temperature of 100° C. The reflux condenser was replaced and the reaction was heated to reflux (195° C.) overnight.

The reaction mixture was cooled to 100° C. and then poured into about 500 mL of ice water, stirred for additional one hour and acidified to a pH of 1.3 with 250 mL of 50% hydrochloric acid. The precipitated white solid was isolated by vacuum filtration and washed with 500 mL of water and 250 mL of 15% hydrogen peroxide. The reaction was further washed with 250 mL of water. The filtered solid was then dried under high vacuum overnight to give 17.9 g of a tan solid.

Yield: 78% Purity: >93% FAB/MS: [M+H]$^+$461.3; [M+NH4]$^+$478.3 Melting Point: 70°–72° C. DSC=70.5° C. (sharp) IR (nujol mull): 2620 (br. w), 1710 (s), 1110 (m) $^1$H (200 MHz, CDCl$_3$): δ7.3 (br. m, 5H), 4.5 (s, 2H), 3.4 (t, J=8 Hz, 2H), 2.3 (t, J=8 Hz, 2H), 1.6 (br. m, 4H), 1.2 (br. s, 34H) $^{13}$C (50 MHz, CDCl$_3$): δ179.6, 138.4, 128.2, 127.5, 127.4, 72.7, 70.4, 34.0, 29.6, 26.1, 24.6

Synthesis of 22-Hydroxydocosanoic Acid 8 (Formula V)

Into a clean, dry 500 ml two neck flask, were charged 2.0 g (1.8 mmole) of 10% palladium on carbon catalyst. The flask is equipped with a stir bar and a rubber septa. In a separate flask, 9.0 g (0.02 moles) of 22-benzyloxy-docosanoic acid were dissolved in 300 mls of 2/1 ethanol/ether by sonicating for 30 minutes. This solution was charged with hydrogen gas (1 atmosphere). The reaction was stirred overnight at room temperature before the solution was recharged with hydrogen. Reaction appeared to be complete after about 40 hours at room temperature.

The contents of the flask were gravity filtered before being washed several times with ethanol. The filtrate was concentrated under vacuum to give 2.4 g of white powder. In addition, the filtered Pd/C catalyst was stirred in boiling ethanol for 30 minutes and filtered while still hot. The filtrate was concentrated under vacuum to give 2.9 g of 22-hydroxy docosanoic acid.

Overall yield: 53% Melting Point: Capillary=95°–96° C. DSC=96.0° C. IR (nujol mull): 2620 (br. w), 1710 (s) $^1$H NMR (200 MHz, CDCL$_3$): d 3.6 (t, 2H), 2.3 (t, 2H), 1.6 (br. m, 4H), 1.2 (br. s, 36H)

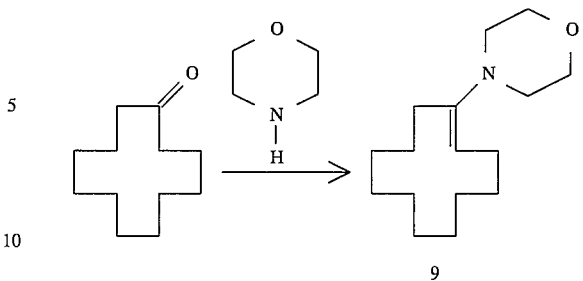

Synthesis of N-Morpholino-1-cyclododecene 9

A 100 mL three neck round bottom flask, equipped with a stir bar, thermometer and a Dean-Stark trap, was charged with 10 g (55 mmoles) of cyclododecanone, 6.7 g (77 mmoles) of morpholine, 40 mL of anhydrous toluene and a catalytic amount of p-toluenesulfonic acid monohydrate. The reaction mixture was refluxed for 48–77 hours. The toluene was removed under vacuum, and the reaction mixture was vacuum distilled to give 5.7 g of N-morpholino-1-cyclododecene (at 160°–168° C./0.5mm) as a 95% pure clear liquid.

IR (neat): 1640 (s) $^1$H NMR (200 MHz, CD$_2$CL$_2$): δ4.3 (t, 1H), 3.6 (t,4H), 2.7 (t,4H), 2.2 (t,2H), 2.0 (m,2H), 1.5 (br.s, 16H) GC: Retention time =11.7 minutes

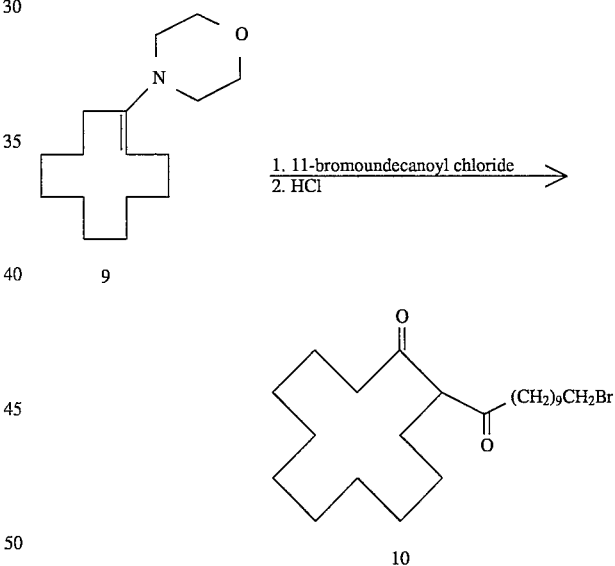

Synthesis of 2-(11-bromoundecanoyl)-cyclododecanone 10

A 50 mL round bottom flask, equipped with a dropping funnel and stir bar, was charged with 5.6 g (21.5 mmoles) of N-morpholino-1-cyclododecene, 2.17 g (21.5 mmoles) of triethylamine and 10 mL of anhydrous toluene. The dropping funnel was charged with 6.0 g (21.5 mmoles) of 11-bromoundecanoyl chloride, and the acid chloride was added dropwise to the reaction mixture at 45° C. After the addition of acid chloride, the reaction mixture was stirred at 75° C. overnight. After the reaction mixture was cooled, 10 mL of 20% hydrochloric acid was added and the reaction mixture was refluxed for an additional 24 hours.

After cooling, the reaction mixture was extracted with 100 mL of methylene chloride and 100 mL of water. The organic layer was collected, dried over magnesium sulfate, filtered and concentrated under vacuum to give 8.6 g of a dark red viscous liquid.

IR (neat): 1705 (br.s) $^1$H NMR (200 MHz, CD$_2$CL$_2$): δ3.5 (t, 1H), 2.4 (t, 2H), 2.2 (apparent m,4H), 1.5 (br, 34H) Cl exchanged [M+H]$^+$=385.2 [M+H]$^+$=429

Synthesis of 23-hydroxy-13-ketotricosanoic Acid 11

A 250 mL round bottom flask, equipped with a condenser and stir bar, was charged with 8.6 g (20 mmoles) of 2-(11-bromoundecanoyl)-cyclododecanone, 4.3 g (78 mmoles) of potassium hydroxide and 100 mL of methanol. The reaction mixture refluxed for 17 hours, and the methanol was removed under vacuum. The resulting solid was dissolved in about 300 mL of water and acidified to a pH of 1 with 100 mL of 10% hydrochloric acid. The acidified solution was filtered, and the filtered solid was dried under high vacuum to give 7.6 g of a brown soft solid.

IR (neat): 3000–3300 (br), 1700 (s) $^1$H NMR (200 MHz, CDCL$_3$): δ3.5 (t,2H), 2.4 (apparent m,6H), 1.5 (br.s,34H) [M+NH3]+=399.2

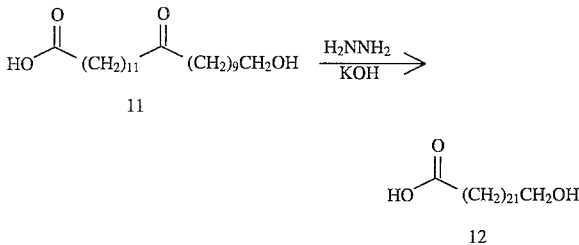

Synthesis of 23-hydroxy tricosanoic Acid 12

A 100 mL three neck round bottom flask, equipped with a overhead stirrer, condenser and a thermometer, was charged with 1.93 g (34.5 mmoles) of powdered potassium hydroxide and 23 mL of anhydrous ethylene glycol. The reaction mixture was heated to 50° C. before 7.0 g (17.2 mmoles) of sodium-23-hydroxy-13-ketotricosanoate and 3.45 g (69 mmoles) of hydrazine monohydrate were added. The reaction was stirred at 143° C. for 2.5 hours before the excess hydrazine and water were distilled off at ~150°–180° C. The reaction was then further refluxed at 195° C. for overnight.

The reaction mixture was cooled to 100° C., poured into 300 mL of ice water and adjusted to a pH of 1.0 with 50% HCl. The precipitated solid was filtered, washed with 400 mL of water and 100 mL of 15% hydrogen peroxide. The precipitate was then dried under high vacuum to yield 5.1 g of tan solid.

IR (Nujol): 3000–3300 (br.), 1700 (s) $^1$H NMR (200 MHz, CDCL$_3$): δ3.3 (t, 2H), 2.3 (t, 2H), 1.6 (br, m, 4H), 1.3 (br. s, 36H) 13C NMR (60 MHz, CDCL$_3$): δ178, 73, 58, 42, 34, 29 (br.), 26, 23

EXAMPLE 3

To establish the preferred parameters of Wolff-Kischner reduction, Example 1 was repeated with various concentrations of ketoacid, hydrazine, and base. Example 1 was also repeated with various reflux times. The results that were obtained are summarized in the table below.

| Test | Conc. Keto Acid in ethylene glycol | Ratio of KOH to Ketoacid | Ratio of Sodium Methoxide to Ketoacid | Ratio of hydrazine to ketoacid | Reflux Time (hrs) | % Conversion into Compound V or IX |
|---|---|---|---|---|---|---|
| | | | Results of Wolff-Kischner Reductions | | | |
| A | 6.5 E - 2M | 2.0 | — | 2.0 | 4 | None |
| B | 4.6 E - 2M | 2.0 | — | 2.0 | 24 | 10 |
| C | 8.0 E - 2M | 2.0 | — | 2.0 | 7 | 9 |
| D | 1.1 E - 1M | — | 2.0 | 2.0 | 24 | 16 |
| E | 1.0 E - 1M | — | 4.0 | 2.0 | 24 | 40 |
| F | 5.5 E - 1M | — | 4.0 | 2.0 | 36 | 43 |
| G | 8.3 E - 1M | 2.0 | — | 4.0 | 20 | 93 |

The results in the table above illustrate that the best results were obtained with concentrations and reflux time employed in test G (increased hydrazine to ketoacid ratio and decreased reflux time).

It should be understood that the specific forms of the invention herein illustrated and described are intended to be representative only. Changes, including but not limited to those suggested in this specification, may be made in the illustrated embodiments without departing from the clear teaching of the disclosure. Accordingly, reference should be made to the following appended claims in determining the full scope of the invention.

What is claimed is:

1. A process of preparing an ω-hydroxy acid, the process comprising the steps of:

(i) preparing an anhydrous mixture comprising:

(a) an enamine having Formula I:

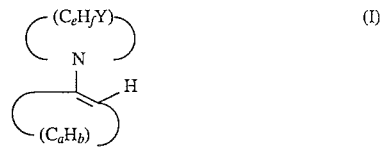

wherein
   a is an integer from 1 to 20,
   b is an integer from 2 to 40,
   e is an integer from 4 to 12,
   f is an integer from 4 to 24, and
   Y is oxygen, nitrogen, or —CH$_2$, (b) a compound having Formula II:

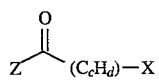

wherein
c is an integer from 1 to 30;
d is an integer from 2 to 60;
X selected from the group consisting of —OH, a halogen atom, OTs, and OMs; and
Z is a halogen atom; and
(c) a base catalyst;
wherein the molar ratio of the enamine to the compound having Formula II is in the range of from about 1:1 to about 1:2;

(ii) reacting the anhydrous mixture obtained in step (i) at a temperature in the range of from about 20° C. to about 150° C., to obtain a first reaction solution;

(iii) quenching the first reaction solution obtained in step (ii) with an aqueous acid and refluxing to obtain a second reaction solution containing a diketone having Formula III:

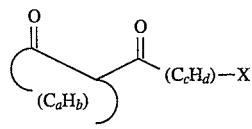

(iv) mixing the diketone having Formula III with a hydroxy-containing inorganic base in a solvent to obtain a third reaction solution;

(v) refluxing the third reaction solution obtained in step (iv) to obtain a fourth reaction solution containing a ketoacid having Formula IV:

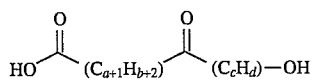

(vi) carrying out a reduction of the diketone having Formula (IV) to obtain the ω-hydroxy acid having Formula V

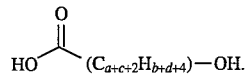

2. The process of claim 1 wherein in step (i) of the process the anhydrous mixture is prepared in two steps carried out in the following order:
(ia) adding the base catalyst to the enamine having Formula (I); and subsequently
(ib) adding the compound having Formula II to the mixture obtained in step (ia).

3. The process of claim 1 wherein the anhydrous mixture further comprises a drying agent.

4. The process of claim 1 wherein steps (i) and (ii) of the process are carried out under an inert gas blanket.

5. The process of claim 1 wherein the anhydrous mixture in step (i) further comprises an organic solvent.

6. The process of claim 1 wherein the amount of the base catalyst in step (i) is in the range of from 0.5 to 5 equivalents based on the amount of the enamine.

7. The process of claim 1 wherein the base catalyst is an organic base.

8. The process of claim 1 wherein the temperature in step (ii) of the process is in the range of from about 25° C. to 150° C.

9. The process of claim 1 wherein in step (iv) the ratio of the hydroxy-containing inorganic base to compound III is in the range of from about 1:1 to about 6:1.

10. The process of claim 1 wherein the reduction in step (vi) is Wolff-Kischner reduction.

11. The process of claim 10 wherein the reflux time is 1 to 48 hours, so that excess hydrazine is distilled off and to assure the decomposition of hydrazone.

12. The process of claim 10 wherein the ratio of ketoacid to hydrazine ratio is 1:8.

13. The process of claim 10 wherein the ratio of the ketoacid to base ratio is in the range of from 1:1 to 1:6.

14. The process of claim 1 wherein the enamine is N-morpholinocyclododecene having Formula 9:

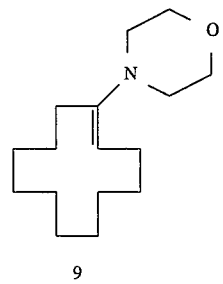

and compound II is 11-bromoundecanoyl chloride.

15. The process of claim 14 wherein the ω-hydroxy acid is 23-hydroxy tricosanoic acid having Formula $HOCH_2(CH_2)_{20}CH_2CO_2H$.

16. The process of claim 1 wherein the ω-hydroxy acid is 22-hydroxydocosanoic acid having Formula $HOCH_2(CH_2)_{19}CH_2CO_2H$.

17. A process of preparing an ω-hydroxy acid, the process comprising the steps of:
(i) preparing an anhydrous mixture comprising:
(a) an enamine having Formula I:

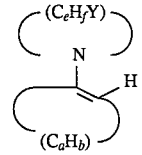

wherein
a is an integer from 1 to 20,
b is an integer from 2 to 40,
e is an integer from 4 to 12,
f is an integer from 4 to 24, and
Y is oxygen, nitrogen or $CH_2$;
(b) a compound having Formula VI:

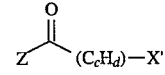

wherein
c is integer from 1 to 30;
d is an integer from 2 to 60;
X' is an alkyl ether or aryl ether; and
Z is a halogen atom,
(c) a base catalyst;
wherein the molar ratio of the enamine to the compound having Formula VI is in the range of from about 1:1 to about 1:2;

(ii) reacting the anhydrous mixture obtained in step (i) at a temperature in the range of from about 20° C. to about 150° C., to obtain a first reaction solution;

(iii) quenching the first reaction solution obtained in step (ii) with an aqueous acid and refluxing to obtain a second reaction solution containing a diketone having Formula VII:

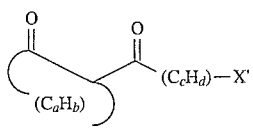

(VII)

(iv) mixing the diketone having Formula VII with a hydroxy-containing inorganic base in a solvent to obtain a third reaction solution;

(v) refluxing the third reaction solution obtained in step (iv) to obtain a fourth reaction solution containing a ketoacid having Formula VIII:

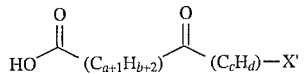

(VIII)

(vi) carrying out a reduction of the diketone having Formula (VIII) to obtain a compound of Formula (IX)

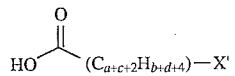

(IX)

(vii) carrying out hydrogenation of the compound having Formula IX to obtain the ω-hydroxy acid having Formula V:

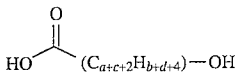

(V)

\* \* \* \* \*